United States Patent [19]

McHugh

[11] Patent Number: 5,710,003
[45] Date of Patent: Jan. 20, 1998

[54] DIAGNOSTIC TEST TO DETERMINE THE MALIGNANCY OF SMOOTH MUSCLE TUMORS

[75] Inventor: Kirk M. McHugh, Sicklerville, N.J.

[73] Assignee: Thomas Jefferson University, Philadelphia, Pa.

[21] Appl. No.: 588,113

[22] Filed: Jan. 18, 1996

[51] Int. Cl.$^6$ .............................. C12Q 1/68; G01N 33/58; C12P 19/34
[52] U.S. Cl. .............................. 435/6; 435/7.1; 435/91.2; 536/24.31
[58] Field of Search .............................. 435/6, 91, 177.3, 435/7.1, 91.2; 536/28, 29, 24.31

[56] References Cited

U.S. PATENT DOCUMENTS 4,683,202   7/1987   Mullis ..................................... 435/91

OTHER PUBLICATIONS

Liaw, D et al. 1993 Am J.Clin. Path. 100(3) 345. Ab. #147.
Kanno et al 1992. Hinyokika Kiyo 38(2) : 189–93.
Miwa, T. et al. 1990 Nucleic Acids Research 18(4) 1263.
Miwa, T. et. al. 1991. Mol. Cell. Biol. 11 pp. 3296–3306.
Clontech Catalog 1995 pp. 26–27.
Chirgwin, et al., "Isolation of Biologically Active Ribonucleic Acid from Sources Enriched in Ribonuclease", *Biochem.*, 1984, 18, 5294–5299.
Erba, et al., "Nucleotide sequence of the human γ cytoskeletal actin mRNA: anomalous evolution of vertebrate non-–muscle actin genes", *Nucleic Acid Research*, 1988, 14, 5275–5295.
Harlow and Lane, Eds., *Antibodies: A Laboratory Manual*, Cold Spring Harbor Press, (1988).
Lazard, et al., "Expression of smooth muscle–specific proteins in myoepithelium and stromal myofibroblasts of normal and malignant human breast tissue", *PNAS USA*, 1993, 90, 999–1003.
Liaw, et al., "Molecular Analysis of Smooth Muscle Isoactin Gene Expression in a Variety of Human Neoplasms", *Am. J. Clin. Path.*, 1993, 100(3), 345, Abstract 147.
McHugh and Lessard, "The Development Expression of the Rat α–Vascular and γ–Enteric Smooth Muscle Isoactins: Isolation and Characterization of a Rat γ–Enteric Actin cDNA", *Mol. Cell. Biol.*, 1988, 8, 5224–5231.
Miwa, et al., "Structure, Chromosome Location, and Expression of the Human Smooth Muscle (Enteric Type) γ–Actin Gene: Evolution of Six Human Actin Genes", *Mol. Cell. Biol.*, 1991, 11, 3296–3306.
Tso, et al., "Isolation and characterization of rat and human glyceraldehyde–3–phosphate dehydrogenase cDNAs: genomic complexity and molecular evolution of the gene", *Nucleic Acid Research*, 1985, 13, 2485–2502.
Ueyama, et al., "Structure of a Human Smooth Muscle Actin Gene (Aortic Type) with a Unique Intron Site", *Mol. Cell. Biol.*, 1984, 4, 1073–1078.

*Primary Examiner*—James Ketter
*Assistant Examiner*—Irem Yucel
*Attorney, Agent, or Firm*—Woodcock Washburn Kurtz Mackiewicz & Norris, LLP

[57] ABSTRACT

The present invention provides methods of diagnosing smooth muscle tumors for malignancy by testing for the expression of γ-smooth muscle isoactin. Diagnostic kits are also provided.

17 Claims, 1 Drawing Sheet

DIAGNOSTIC TEST TO DETERMINE THE MALIGNANCY OF SMOOTH MUSCLE TUMORS

FIELD OF THE INVENTION

The present invention is related to methods of diagnosing malignant smooth muscle tumors.

BACKGROUND OF THE INVENTION

Leiomyomas are tumors composed of smooth muscle cells which can range from clearly benign leiomyoma (fibroids) to the malignant leiomyosarcoma. Intermediate variants have also been identified and are termed "smooth muscle tumors of uncertain malignant potential". These may include cellular leiomyomas. Leiomyomas are responsible for at least one third of all gynecological admissions to hospitals and occur in one in four women in active reproductive life. Leiomyomas are most common in women of the age of 30–50 and are more common in blacks. Leiomyomas are the most common tumors found in women and occur in 20–30% of the women older than 30 years of age.

Leiomyosarcomas are more rare than leiomyomas and occur equally in pre- and post-menopausal women with a peak in occurrence at 40–60 years of age. 5% or less of all uterine malignancies are sarcomas, with leiomyosarcomas representing 25% of all uterine sarcomas. One out of every 800 smooth muscle tumors of the uterus is a leiomyosarcoma. Leiomyosarcomas present with an incidence rate of slightly less than 1 in every 100,000 women 20 years or older. Leiomyosarcomas have a high incidence of recurrence and possess the potential to metastasize throughout the abdominal cavity. Five year survival averages 40%.

Although leiomyomas and leiomyosarcomas are most prevalent in the uterine smooth muscle, they can occur in any organ system which possesses smooth muscle. The second highest incidence of occurrence for these tumor types is in the gastrointestinal tract. Although rare in absolute numbers, leiomyomas represent one of the most common benign tumors of the stomach, while gastric leiomyosarcomas represent approximately 2% of all malignant tumors that occur in the stomach.

At present, the histologic diagnosis of leiomyosarcomas and leiomyomas is difficult. A tumor is generally diagnosed as a leiomyosarcomas if the clinician observed more than 10 mitoses per 10 high-power fields (HPF) with or without cellular atypia or 5 to 10 mitoses per HPF with cellular atypia. A tumor is diagnosed to have uncertain malignant potential if 5 to 10 mitoses per HPF are observed with no cellular atypia. Tumors exhibiting less than 5 mitoses per HPF are diagnosed benign. The present invention provides a valuable molecular adjunct to these customary histologic analysis. The present invention can help to differentiate which smooth muscle tumors are benign versus those that are malignant.

SUMMARY OF THE INVENTION

At present, the histologic diagnosis of benign versus malignant smooth muscle tumors is exceedingly difficult. In addition, the diagnosis of smooth muscle tumors of uncertain malignant potential remain equivocal since these tumors possess histologic characteristics of both benign and malignant tumors. Without a definitive diagnosis prudence tended to dictate treatment protocols including surgical removal of the tumor and surrounding tissue and radiation therapy, despite the fact that a possibility existed that the tumor was actually benign.

The present invention provides a method of more definitively diagnosing the malignant potential of a smooth muscle tumor which will eliminate many unnecessary surgeries and other treatments.

In accordance with the present invention is provided methods of diagnosing the malignancy of smooth muscle tumors by obtaining a biopsy from a smooth muscle tumor and detecting expression of human γ-smooth muscle isoactin whereby expression of human γ-smooth muscle isoactin indicates that the smooth muscle tumor is benign.

In some embodiments of the present invention methods of diagnosing smooth muscle tumors comprise obtaining a biopsy from a smooth muscle tumor and obtaining cDNA from the biopsy. The cDNA is contacted with a primer pair comprising a specific primer and a common primer. The specific and common primers are complementary to non-contiguous regions of the human γ-smooth muscle isoactin gene. The region of the gene flanked by the primer pair is amplified and the presence or absence of amplification product is detected wherein the presence of amplification product indicates that the tumor is benign.

Kits are also provided by the present invention comprising primers complementary to two non-contiguous regions of the human γ-smooth muscle isoactin gene and written instructions detailing the protocol to be followed.

DETAILED DESCRIPTION OF THE INVENTION

Figure 1A:
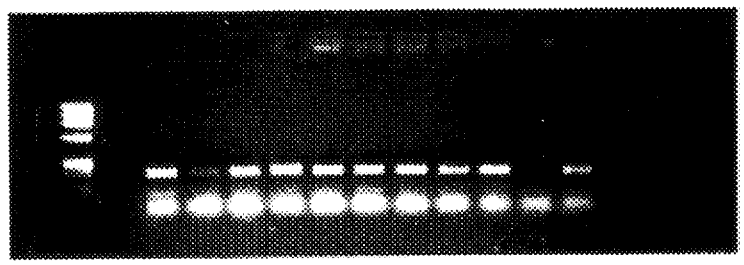
FIG. 1A is a photograph of a 1% agarose gel. PCR amplification products from various tissue samples were run. Expression of γ-smooth muscle isoactin mRNA was evidenced by a band at approximately 204 bp.

The present invention satisfies a long felt need for a method of definitively diagnosing benign versus malignant smooth muscle tumors. It has been found that benign smooth muscle tumors express human γ-smooth muscle isoactin while malignant smooth muscle tumors do not. This discovery can be used to distinguish benign from malignant smooth muscle tumors.

Thus, in accordance with methods of the present invention, a biopsy of a smooth muscle tumor is obtained. As this method will generally be used as an adjunct to traditional pathologic tests, surgical resections or biopsies already performed by clinicians can be used as a sample.

Tests are then performed with the biopsy to determine whether human γ-smooth muscle isoactin is expressed by the tumor cells. This may be achieved in any number of ways known to those skilled in the art to determine whether a particular protein is expressed by a cell or tissue. The production of monoclonal antibodies can be performed by standard techniques known to those skilled in the art of antibody production. Harlow and Lane ed., *Antibodies: A Laboratory Manual*, Cold Spring Harbor (1988), incorporated by reference herein in its entirety, describes laboratory techniques for the preparation of monoclonal antibodies. Briefly, production of monoclonal antibodies is performed by immunizing mice with an appropriate γ-smooth muscle isoactin antigen. The sequence of γ-smooth muscle isoactin DNA is known. Miwa, et al., *MOl. Cell. Biol.*, 11:3296–3306

(1991). One skilled in the art may prepared appropriate antigens based upon DNA, cDNA or amino acid sequences of γ-smooth muscle isoactin or by isolation and purification of the naturally-occuring protein. The cDNA and amino acid sequence of γ-smooth muscle isoactin are set forth as SEQ ID NOS: 1 and 2, respectively. Spleen cells from the immunized mice are isolated and fused with myeloma cells. Thereafter the clones are screened by ELISA assays and positive clones selected and expanded for analysis. γ-Smooth muscle isoactin-specific monoclonal antibodies may then be used to detect expression of γ-smooth muscle isoactin protein by 2-dimensional gel electrophoresis and Western blot analysis designed to detect the presence of the protein. In addition, alternative tests may be run to detect RNA encoding the protein such as, for example, Northern blot analysis.

In one embodiment of the present invention, RNA is extracted from the biopsy in accordance with standard methods known to those skilled in the art. Generally, frozen tissue is homogenized, digested with enzyme, and then RNA is extracted using chloroform followed by isopropanol precipitation.

Thereafter, cDNA is prepared using extracted RNA as a template and amplification is performed. Amplification can be performed using well known polymerase chain reaction (PCR) techniques. The PCR primers are chosen to be complementary to non-contiguous regions of the human γ-smooth muscle isoactin gene. The first primer, the "specific primer", is preferably complementary to a region of the 3' or 5' untranslated region, both of which are unique regions of the human γ-smooth muscle isoactin cDNA. For example, the primer 5'- CAT GAC TGG TAA CAG AGT AGT -3' (SEQ ID NO:3) may serve as a specific primer in certain methods of the present invention. The 3' untranslated region of the human γ-smooth muscle isoactin cDNA is bases 1186 through 1275 of SEQ ID NO: 1. The 5' untranslated region of the human γ-smooth muscle isoactin cDNA is bases 1 through 54 of SEQ ID NO: 1. The remainder of the sequence set forth in SEQ ID NO: 1 is the coding region. Primers which are complementary to a region of cDNA hybridize with the cDNA with specificity, i.e. G-C and A-T binding pairs. While generally specificity need not be absolute and may be from about 90 to about 100% specificity, ideally primers of the present invention are completely complementary to the cDNA region to which they are intended to hybridize.

The second primer, or "common primer", need not be specific to the human γ-smooth muscle isoactin gene but rather, may be non-specific in that the second primer may cross-react with other actin isoforms. Thus, while certain portions of the coding region of human γ-smooth muscle isoactin gene are found in other actin isoforms these regions may, nonetheless, be selected for purposes of the second primer. Of course, the primer may also be complementary to the 3' or 5' untranslated region. In some embodiments of the present invention the primer 5'- AGA GCG GAA GTA CTC AGT CTG -3' (SEQ ID NO:4) may serve as the second primer.

It is preferred in methods of the present invention that the primers are each at least about 15 base pairs in length. Primers having about 21 base pairs are preferred in some embodiments. In still other embodiments of the present invention the primers are at least about 25 base pairs in length. Primers can be prepared by methods known to those skilled in the art, such as by solid state synthesis.

In some embodiments of the present invention it may be desirable to label primers used in methods of the present invention with a detectable label as this may facilitate detection of the amplification product. Detectable labels include fluorescent labels, radiolabels and chemoluminescent labels.

Primers of the present invention are designed to amplify a region of human γ-smooth muscle isoactin cDNA and thus must be complementary to different regions of the γ-smooth muscle isoactin gene. In some preferred embodiments of the present invention, the primers flank a unique region about 88 base pairs in length, encompassing the entire 3' untranslated region of human γ-smooth muscle isoactin cDNA. In other preferred embodiments of the present invention, the amplification product is prepared by using primers flanking a region of the cDNA at least about 50 base pairs in length. In still other embodiments of the present invention the amplification product is prepared using primers flanking a region of the cDNA at least about 150 base pairs in length. In further embodiments of the invention the amplification product is prepared using primers flanking a region of the cDNA at least about 200 base pairs in length. In still further embodiments of the invention the amplification product is prepared using primers flanking a region of the cDNA at least about 500 base pairs in length. In yet other embodiments of the present invention the amplification product comprises the entire 1280 base pair γ-smooth muscle isoactin cDNA.

Following amplification the presence or absence of the amplification product is detected. Any of the known methods used to detect DNA fragments may be employed. Use of detectable label will facilitate identification in many instances.

Agarose gel electrophoresis may be used to separate and detect the amplification product. If the product is unlabeled, the size of the amplification product should generally be known. Column chromatography may also be used to detect amplification products. Of course, other methods of identification which will be apparent to those skilled in the art may also be used. Detectable label may be particularly useful for automated applications of methods of the present invention. For instance, a sample may be run to detect the presence or absence of labeled amplification product using high performance liquid chromatography (HPLC) and results may be recorded electronically.

In accordance with methods of the present invention, tests may include a positive control. A gene which is universally expressed in all tissues including benign and malignant smooth muscle tumors can be selected and a portion amplified. For example, expression of glyceraldehyde phosphate dehydrogenase (GAPDH) may be used as a positive control. A second positive control can also be included in which γ-smooth muscle isoactin is known to be expressed. For example, a parallel test using human bladder smooth muscle which is known to express γ-smooth muscle isoactin, can be run.

Kits may be prepared in accordance with the present invention. Kits of the present invention should include at least one primer pair for amplification of a region of the human γ-smooth muscle isoactin gene, and written instructions for running the diagnostic test and interpreting the results. Kits may also include reagents for running positive and/or negative controls.

The following examples are illustrative and should not be considered limiting of the present invention.

EXAMPLE 1

Library Screening A 5' STRETCH PLUS λgt11 human stomach cDNA library was plated under the conditions provided by the supplier (Clonetech Laboratories, Inc.). Approximately 100,000 clones were screened with a universal isoactin cDNA probe derived from the Pst 1 fragment of the pRγSM-11 clone as previously described. McHugh and Lessard, *Mol. Cell. Biol.*, 8:5224–5231 (1988). Purified phage DNA was isolated from positive clones and characterized by restriction enzyme analysis. Two novel clones designated pHγSM-1 and pHαSM-2 were identified for subcloning and further sequence analysis. An Eco R1/Xmn 1 3' untranslated region restriction fragment of approximately 100 bp was isolated from the pHγSM-1 clone, and an Eco R1/Hpa II 3' untranslated region restriction fragment of approximately 200 bp was isolated from the pHαSM-2 clone. Both restriction fragments were subcloned into the Bluescript SK vector and sequenced using the SP6 and T7 primers as outlined by the supplier (Stratagene). Positive identification of the subclones was performed by direct sequence comparison to the human γ-smooth muscle isoactin gene; Miwa, et al., *Mol. Cell. Bio.*, 11:3296–3306 (1991); and the human α-smooth muscle isoactin gene; Ueyama, et al., *Mol. Cell. Biol.*, 4:1073–1078 (1984). cDNA subclones which were specific for the human γ-smooth muscle and human α-smooth muscle isoactins were isolated and designated pHγSM-3' UT-EX and pHαSM-3' UT-EH, respectively. The specificity of the pHγSM-3' UT-EX and pHαSM-3' UT-EH subclones was verified by northern blot analysis of 20 µg of total cellular RNA (tcRNA) isolated from adult rat liver, adult rat stomach, adult human stomach, and adult human uterus under the conditions described below.

EXAMPLE 2

Northern Blot Analysis

A total of 32 human neoplasms and 29 normal tissues were collected from surgical resections, immediately frozen in liquid nitrogen, and stored at −70° C. until RNA isolation. tcRNA was isolated from 1.2 grams or less of tissue according to the methods of Chirgwin. Chirgwin, et al., *Biochem.*, 18:5294–5299 (1984). tcRNA was quantitated spectrophotometrically and visually confirmed by agarose/formaldehyde gel electrophoresis in the presence of 100 µg/ml ethidium bromide. Northern blot analysis was performed on 20 µg or less of tcRNA using 2% agarose/formaldehyde gels and Biotrans nylon membranes (ICN Pharmaceuticals, Inc.). Individual northern blots were sequentially probed with the human γ-smooth muscle isoactin cDNA (pHγSM-3' UT-EX), the human α-smooth muscle isoactin cDNA (pHαSM-3' UT-EH), the human β-cytoplasmic isoactin cDNA; Erba, et al., *Nucleic Acid Research*, 14:5275–5295 (1988); the human γ-cytoplasmic isoactin cDNA; Erba, et al., *Nucleic Acid Research*, 14:5275–5295 (1988); and the universal isoactin cDNA; McHugh and Lessard, *Mol. Cell. Biol.*, 8:5224–5231 (1988) as previously described. All blots were normalized to glyceraldehyde phosphate dehydrogenase (GAPDM) expression. Tso et al., *Nuc. Acids Res.*, 13:2485–2502 (1985). Each probe was labelled by random priming to a specific activity of at least 1×10⁸ DPM/µg/ml.

EXAMPLE 3

Quantitative Analysis

Northern blots were exposed to Kodak X-Omat AR film and multiple exposures of each northern blot were quantitated in the linear range using an LKB Ultrascan XL Enhanced Laser Densitometer and the Gelscan XL program. Standard Gelscan XL program parameters were established for the initial series of quantitation and maintained for the remainder of the blots analyzed. The quantitation values reported represent an average of multiple scannings of multiple blots to eliminate a variety of blot and/or band inconsistencies. The various quantitation values obtained for the blots were normalized to a standard specific activity, exposure time, and GAPDH expression.

EXAMPLE 4

Immunohistochemical Analysis

Specimens displaying instructive patterns of isoactin gene expression were processed for standard immunohistologic analysis with a monoclonal antibody specific for the α-smooth muscle isoactin (Clone 14A) and a monoclonal antibody which was panreactive for all muscle actins (Clone HHF35) as outlined by the supplier (Dako Corporation). Positive controls were included in each run.

EXAMPLE 5

Northern Blot Analysis with Smooth Muscle and Cytoplasmic Isoactin cDNA

Northern blot analysis was performed as described in Example 2 using the human γ-smooth muscle isoactin, human α-smooth muscle isoactin, human β-cytoplasmic isoactin, and human γ-cytoplasmic isoactin specific cDNA probes.

A specific single band of 1.2 kb was observed for the γ-smooth muscle isoactin, 1.4 kb for the α-smooth muscle isoactin, and 2.2 kb each for both the β-cytoplasmic and γ-cytoplasmic isoactins. The results of this analysis are summarized in Table 1.

TABLE 1

Relative Expression of γ-Smooth Muscle, α-Smooth Muscle, β-Cytoplasmic and γ-Cytoplasmic Isoactin Gene Expression in Normal and Neoplastic Human Tissues

| SAMPLE | γ-SM | α-SM | β-CYTO | γ-CYTO |
|---|---|---|---|---|
| normal lung 1 | 0.72 | — | 4.6 | 0.70 |
| normal lung 2 | 0.49 | — | 3.4 | 0.55 |
| normal lung 3 | 2.1 | 0.14 | 9.2 | 0.80 |
| normal lung 4 | — | — | 1.7 | 0.77 |
| normal lung 5 | — | — | 2.3 | 0.93 |
| normal pancreas | — | — | 2.2 | 1.3 |
| normal pancreas | — | — | 4.8 | 0.53 |
| normal spleen | — | — | 32 | 2.4 |
| normal spleen - mod. congestion | — | 0.21 | 5.0 | 1.5 |
| normal skin | — | — | 0.82 | 1.7 |
| myxoid liposarcoma | — | — | 3.1 | 2.8 |
| fibroliposarcoma - myxoid changes | — | — | 2.8 | 7.6 |
| normal kidney 1 | — | — | 2.7 | 0.58 |
| normal kidney 2 | — | — | 2.6 | 1.8 |
| normal kidney 3 | — | — | 1.8 | 0.99 |
| oncocytoma | — | 0.03 | 2.2 | 0.31 |
| normal colon | 11 | 0.31 | 3.4 | 0.76 |
| normal colonic mucosa | 16 | 0.18 | 11 | 0.58 |
| adenocarcinoma - colon | 0.15 | 0.05 | 6.7 | 1.1 |
| normal stomach 1 | 1.7 | 0.42 | 6.1 | 0.64 |
| normal stomach 2 | 1.1 | 0.49 | 3.7 | 0.60 |
| normal stomach 3 | 23 | 0.34 | 6.5 | 0.27 |
| normal stomach 4 | 221 | 0.59 | 15 | 0.59 |
| malignant stromal tumor stomach | — | — | 4.3 | 1.9 |
| gastric Schwanoma | — | — | 0.25 | 0.83 |
| normal thyroid 1 | — | — | 2.3 | 2.8 |
| normal thyroid 2 | 0.88 | 0.10 | 13 | 1.9 |
| thymoma | 0.28 | 0.15 | 15 | 3.1 |
| thyroid carcinoma | — | — | 2.3 | 2.8 |
| normal breast | — | — | 0.17 | 2.2 |
| normal skeletal muscle - breast | — | — | 0.01 | 0.02 |

TABLE 1-continued

Relative Expression of γ-Smooth Muscle, α-Smooth Muscle, β-Cytoplasmic and γ-Cytoplasmic Isoactin Gene Expression in Normal and Neoplastic Human Tissues

| SAMPLE | γ-SM | α-SM | β-CYTO | γ-CYTO |
|---|---|---|---|---|
| normal skeletal muscle | — | — | 0.01 | 0.02 |
| breast mass | — | — | 6.4 | 6.8 |
| infiltrating duct. carc.-breast 1 | 0.17 | 0.03 | 2.7 | 0.38 |
| infiltrating duct. carc.-breast 2 | — | 0.05 | 3.6 | 0.38 |
| infiltrating duct. carc.-breast 3 | — | — | 2.3 | 0.93 |
| infiltrating duct. carc.-breast 4 | — | — | 1.1 | 0.99 |
| infiltrating duct. carc.-breast 5 | — | — | 4.6 | 0.46 |
| normal uterus 1 | 29 | 0.83 | 19 | 1.2 |
| normal uterus 2 | 52 | 0.89 | 6.6 | 0.31 |
| normal uterus 3 | 63 | 2.7 | 14 | 0.78 |
| normal uterus 4 | 98 | 1.2 | 8.7 | 1.0 |
| normal uterus 5 | 17 | 1.5 | 11 | 4.0 |
| leiomyoma - uterus 1 | 3.2 | 0.31 | 17 | 0.81 |
| leiomyoma - uterus 2 | 34 | 0.83 | 10 | 0.74 |
| leiomyoma - uterus 3 | 45 | 0.70 | 8.7 | 1.3 |
| leiomyoma - uterus 4 | 2.2 | 0.58 | 7.9 | 1.2 |
| leiomyoma - uterus 5 | 4.9 | 0.36 | 5.3 | 1.7 |
| leiomyoma - uterus 6 | 72 | 1.5 | 8.8 | 2.0 |
| leiomyoma - pelvis | 32 | 2.6 | 16 | 1.4 |
| cellular leiomyoma - uterus 1 | 5.5 | 0.93 | 15 | 1.1 |
| cellular leiomyoma - uterus 2 | 5.0 | 0.84 | 27 | 1.6 |
| cellular leiomyoma - uterus 3 | 5.8 | 0.55 | 13 | 1.2 |
| leiomyosarcoma - uterus 1 | — | 1.4 | 9.0 | 0.78 |
| leiomyosarcoma - uterus 2 | — | 1.9 | 71 | 5.9 |
| leiomyosarcoma - uterus 3 | — | 1.3 | 50 | 8.4 |
| ovarian fibroma | — | — | 11 | 16 |
| papillary serous carcinoma | — | — | 3.4 | 0.52 |
| metastatic neuroendocrine carcinoma - liver | — | — | 4.0 | 0.53 |
| well differentiated chordoma | — | — | 0.85 | 0.77 |

NOTE. Abbreviations are γ-smooth muscle (γ-SM), α-smooth muscle (α-SM), β-cytoplasmic (β-CYTO), and γ-cytoplasmic (γ-CYTO) isoactins.

EXAMPLE 6

Expression of γ-Smooth Muscle and α-Smooth Muscle Isoactin in Neoplastic Tissue

Northern blot analysis was performed as described in Example 2 to detect the expression of the γ-smooth muscle and α-smooth muscle isoactins in several neoplastic tissues derived from or known to contain smooth muscle. As shown in Table 1, expression of γ- and α-smooth muscle isoactin was expressed in tissue including uterine leiomyomas, pelvic leiomyoma, and uterine cellular leiomyomas. In addition, γ-smooth muscle and α-smooth muscle isoactin expression was detected in 1/1 thymoma and 1/1 adenocarcinoma of the colon.

EXAMPLE 7

Histologic Analysis of Neoplastic Tissue

Histologic analysis was performed as described in Example 4. Histologic analysis of the thymoma revealed that the smooth muscle isoactin expression was limited to several large blood vessels associated with the tissue. Histologic analysis of the adenocarcinoma of the colon revealed that the smooth muscle isoactin expression was limited to normal mucosal smooth muscle associated with the specimen. Independent expression of the α-smooth muscle isoactin was observed in 3/3 uterine leiomyosarcomas, 1/1 oncocytoma of the kidney, and 2/5 infiltrating ductal carcinomas of the breast. Histologic analysis of the positive infiltrating ductal carcinomas of the breast revealed that the α-smooth muscle isoactin expression was limited to the associated vasculature and myoepithelial cells. This observation is consistent with prior studies; Lazard, et al., *PNAS USA*, 90:999–1003 (1993); which have demonstrated that myoepithelial cells express α-smooth muscle isoactin. Histologic analysis of the uterine leiomyomas, uterine cellular leiomyomas, uterine leiomyosarcomas and oncocytoma of the kidney revealed distinct α-smooth muscle isoactin expression throughout the parenchyma of all four tumor types. Interestingly, leiomyosarcomas differentially express the α-smooth muscle isoactin in the absence of any apparent γ-smooth muscle isoactin expression. No expression of the smooth muscle isoactins was detected in a malignant stromal tumor of the stomach, gastric schwannoma, myxoid liposarcoma, fibrolipoma, papillary serous carcinoma, ovarian fibroma, metastatic neuroendocrine carcinoma of the liver, and low grade chordoma.

EXAMPLE 8

Quantitative Analysis of Isoactin Expression

Quantitative analysis demonstrated an interesting pattern of isoactin gene expression in normal versus neoplastic uterine tissues. The γ-smooth muscle isoactin showed a steady 50-fold decrease in expression to undetectable levels as one progressed from normal uterus through leiomyoma and cellular leiomyoma to leiomyosarcoma. By comparison, expression of the α-smooth muscle isoactin remained relatively constant in both normal and neoplastic uterine tissues. Expression of the β-cytoplasmic and γ-cytoplasmic isoactins also remained relatively constant in normal uteri, leiomyomas and cellular leiomyomas. A 3.5 fold increase in expression for both the β-cytoplasmic and γ-cytoplasmic isoactins was observed in leiomyosarcomas. Results are shown in Table 2.

TABLE 2

Average Relative Isoactin Gene Expression in Normal and Neoplastic Uterine Tissues

| | γ-SM | α-SM | β-CYTO | γ-CYTO |
|---|---|---|---|---|
| Normal Uterus | 52 ± 14 | 1.4 ± 0.3 | 12 ± 2.2 | 1.5 ± 0.7 |
| Leiomyoma | 27 ± 12 | 0.7 ± 0.18 | 9.6 ± 1.6 | 1.3 ± 0.2 |
| Cellular Leiomyoma | 5.4 ± 0.2 | 0.77 ± 0.12 | 18 ± 4.4 | 1.3 ± 0.2 |
| Leiomyosarcoma | 0.0 | 1.5 ± 0.19 | 43 ± 18 | 5.0 ± 2.2 |

All values are reported as relative isoactin gene expression ± standard error of the mean (SEM). Abbreviations are γ- smooth muscle (γ-SM), α-smooth muscle (α-SM), β-cytoplasmic (β-CYTO), and γ-cytoplasmic (γ-CYTO) isoactins.

These results indicate a significant shift from a predominance of muscle-specific isoactins in normal uterine tissue to a predominance of nonmuscle isoactins in malignant uterine tissue perhaps reflecting a progressive loss of cellular differentiation. This analysis also revealed that uterine leiomyomas display a mixed pattern of γ-smooth muscle isoactin expression with three specimens maintaining relatively high levels of expression (ie: more similar to normal uterus) and three specimens showing a dramatic decrease in γ-smooth muscle isoactin expression (ie: more similar to cellular leiomyomas). Reexamination of these specimens indicated a correlation between low levels of γ-smooth muscle isoactin gene expression and the degree of cellularity observed in the various leiomyomas.

EXAMPLE 9

RNA Isolation

Approximately 0.5–1.2 grams of frozen tissue was homogenized in RNAzol B (Biotecx Laboratories, Inc. city, state) (2 mls/100 g tissue) and then chloroform extracted once (0.3 mls chloroform/2 mls homogenate). The upper aqueous phase was removed and isopropanol precipitated by standard techniques. The resulting RNA pellet was washed once in 75% ethanol, ethanol precipitated (100% ethanol), dried and resuspended in sterile water. The yield of total cellular RNA was determined spectrophotometrically and recorded.

EXAMPLE 10

First Strand Synthesis 2.0 μg of total cellular RNA was placed in 9.0 μl of sterile water and denatured by incubation at 65° for 5 minutes. The sample was chilled on ice and 10 ml of "RT-MIX" (BRL, 5X RT buffer, 0.1M DTT, 200 μM dNTP mix, 25 μM Primer 1) was added to each sample. Samples were incubated at 37° for 10 minutes. 1 μl of reverse transcriptase (Superscript II, BRL) was added to each sample and incubated at 37° for 1 hour. Samples were then stored on ice until PCR analysis.

EXAMPLE 11

PCR Analysis

Each sample was serially diluted 1:100 in sterile water. 2 μl of each is 1:100 dilution was used for PCR analysis. 18 ml of "PCR Mix" was added to each 2 μl sample and overlayed with mineral oil. "PCR Mix" includes 25 μM Primer 1, 25 μM Primer 2, 1.25 μM dNTP mix, 25 mM MgCl$_2$, 10X Taq Polymerase buffer, 1 unit Taq Polymerase (Promega). PCR reaction conditions were:

94° C.—5 minutes
94° C.—30 seconds
60° C.—30 seconds—for 25 cycles
72° C.—30 seconds
72° C.—5 minutes

EXAMPLE 12

Sample Analysis

Figure 1B:
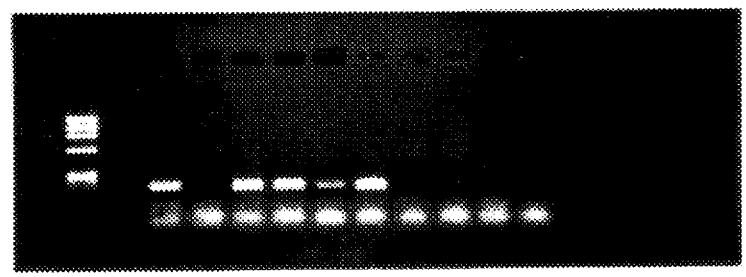
FIG. 1B is a photograph of a 1% agarose gel. PCR amplification products from various tissue samples were run. Expression of γ-smooth muscle isoactin mRNA was evidenced by a band at approximately 204 bp.

Each sample was analyzed by standard 1% agarose gel electrophoresis for the presence or absence of a 204 base pair fragment. The presence of the 204 base pair fragment meant that the human γ-smooth muscle isoactin gene was expressed in that specimen and hence the tumor is benign. The absence of the 204 base pair fragment means the γ-smooth muscle isoactin gene was not expressed and hence the tumor is malignant. A positive control was run which includes human bladder smooth muscle. This sample gave a 204 base pair fragment upon analysis. Results are shown in FIG. 1A and FIG. 1B and summarized in Table 3. Lane 1 and 14 are φ174 HaeIII molecular weight markers having molecular weights of 1353, 1078, 873, 603 and 310 base pairs. Lanes 4–11, 13, 18–21 show results from non-malignant tissue samples. In each of these samples γ-smooth muscle isoactin mRNA was expressed (designated "+"). Lanes 22–25 show results from malignant tissue samples. In each of these samples γ-smooth muscle isoactin mRNA was not expressed (designated "−"). Positive controls were run in lanes 3 and 16. The positive control was RNA from human bladder. Negative controls were run in lanes 12 and 17. The negative control was normal human skin.

TABLE 3

| Lane | Sample | Result |
|---|---|---|
| 1 | φX174 Hae III digest | |
| 2 | blank | |
| 3 | human bladder RNA | + |
| 4 | uterine leiomyoma 1 | + |
| 5 | pelvic leiomyoma 1 | + |
| 6 | normal uterus 1 | + |
| 7 | normal uterus 2 | + |
| 8 | leiomyoma 2 | + |
| 9 | normal uterus 3 | + |
| 10 | leiomyoma 3 | + |
| 11 | normal uterus 4 | + |
| 12 | normal human skin | − |
| 13 | leiomyoma 4 | + |
| 14 | φX174 Hae III digest | |
| 15 | blank | |
| 16 | human bladder RNA | + |
| 17 | rat liver RNA | − |
| 18 | cellular leiomyoma 1 | + |
| 19 | cellular leiomyoma 2 | + |
| 20 | normal uterus | + |
| 21 | cellular leiomyoma 3 | + |
| 22 | leiomyosarcoma 1 | − |
| 23 | leiomyosarcoma 2 | − |
| 24 | leiomyosarcoma 3 | − |
| 25 | leiomyosarcoma 4 | − |

What is claimed is:

1. A method of diagnosing the malignancy of smooth muscle tumors comprising obtaining a biopsy from a smooth muscle tumor and detecting the presence or absence of the expression of human γ-smooth muscle isoactin whereby expression of human γ-smooth muscle isoactin indicates that the smooth muscle tumor is benign.

2. The method of claim 1 whereby the presence or absence of expression is detected by preparing cDNA from said biopsy; contacting the cDNA with a primer pair comprising a specific primer and a common primer, wherein the primer pair is complementary to two non-contiguous regions of human γ-smooth muscle isoactin cDNA; amplifying the region of cDNA flanked by the primer pair; and detecting the presence or absence of amplification product wherein the presence of amplification product indicates expression of human γ-smooth muscle isoactin.

3. The method of claim 2 wherein said specific primer is complementary to a portion of the 3' untranslated region of SEQ ID NO: 1.

4. The method of claim 2 wherein the specific primer is complementary to at least 15 contiguous nucleotides of the 3' untranslated region of SEQ ID NO: 1.

5. The method of claim 2 wherein the specific primer is complementary to at least 21 contiguous nucleotides of the 3' untranslated region of SEQ ID NO: 1.

6. The method of claim 2 wherein the specific primer is complementary to at least 30 contiguous nucleotides of the 3' untranslated region of SEQ ID NO: 1.

7. The method of claim 2 wherein the specific primer is complementary to at least 50 contiguous nucleotides of the 3' untranslated region of SEQ ID NO: 1.

8. The method of claim 2 wherein the specific primer is complementary to the 3' untranslated region of SEQ ID NO: 1.

9. The method of claim 2 wherein the specific primer is complementary to a portion of the 5' untranslated region of SEQ ID NO: 1.

10. The method of claim 2 wherein the common primer is complementary to a portion of the coding region of SEQ ID NO: 1.

11. The method of claim 2 wherein the primer pair flanks at least 50 contiguous nucleotides of SEQ ID NO: 1.

12. The method of claim 2 wherein the primer pair flanks at least 100 contiguous nucleotides of SEQ ID NO: 1.

13. The method of claim 2 wherein the primer pair flanks at least 200 contiguous nucleotides of SEQ ID NO: 1.

14. The method of claim 2 wherein the primer pair flanks at least 500 contiguous nucleotides of SEQ ID NO: 1.

15. The method of claim 2 wherein at least one primer is detectably labeled.

16. The method of claim 2 wherein the detectable label is selected from the group consisting of a fluorophore, a radiolabel and a chemiluminescent label.

17. The method of claim 1 wherein detection of the expression of human γ-smooth muscle isoactin is performed by Western immunoblot analysis.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

(A) LENGTH: 1275 base pairs
(B) TYPE: nucleic acid
(C) STRANDEDNESS: single
(D) TOPOLOGY: unknown (ii) MOLECULE TYPE: cDNA (ix) FEATURE:
(A) NAME/KEY: CDS
(B) LOCATION: 55..1186

(xi) SEQUENCE DESCRIPTION: SEQ ID NO:1:

```
GAACCTCTCA TACCCTCGGT GCTCCAGTCC CCAGCTCACT CAGCCACACA CACC ATG      57
                                                             Met
                                                              1

TGT GAA GAG GAG ACC ACC GCG CTC GTG TGT GAC AAT GGC TCT GGC CTG     105
Cys Glu Glu Glu Thr Thr Ala Leu Val Cys Asp Asn Gly Ser Gly Leu
      5                  10                  15

TGC AAG GCA GGC TTC GCA GGA GAT GAT GCC CCC CGG GCT GTC TTC CCC     153
Cys Lys Ala Gly Phe Ala Gly Asp Asp Ala Pro Arg Ala Val Phe Pro
         20                  25                  30

TCC ATT GTG GGC CGC CCT CGC CAC CAG GGT GTG ATG GTG GGA ATG GGC     201
Ser Ile Val Gly Arg Pro Arg His Gln Gly Val Met Val Gly Met Gly
     35                  40                  45

CAG AAA GAC AGC TAT GTG GGG GAT GAG GCT CAG AGC AAG CGA GGG ATC     249
Gln Lys Asp Ser Tyr Val Gly Asp Glu Ala Gln Ser Lys Arg Gly Ile
 50                  55                  60                  65

CTA ACT CTC AAA TAC CCC ATT GAA CAC GGC ATC ATC ACC AAC TGG CAT     297
Leu Thr Leu Lys Tyr Pro Ile Glu His Gly Ile Ile Thr Asn Trp His
             70                  75                  80

GAC ATG GAG AAG ATC TGG CAC CAC TCC TTC TAC AAT GAG CTG CGT GTA     345
Asp Met Glu Lys Ile Trp His His Ser Phe Tyr Asn Glu Leu Arg Val
         85                  90                  95

GCA CCT GAA GAG CAC CCC ACC CTG CTC ACA GAG GCT CCC CTA AAT CCC     393
Ala Pro Glu Glu His Pro Thr Leu Leu Thr Glu Ala Pro Leu Asn Pro
    100                 105                 110

AAG GCC AAC AGG GAA AAG ATG ACC CAG ATC ATG TTT GAA ACC TTC AAT     441
Lys Ala Asn Arg Glu Lys Met Thr Gln Ile Met Phe Glu Thr Phe Asn
115                 120                 125

GTC CCT GCC ATG TAC GTC GCC ATT CAA GCT GTG CTC TCC CTC TAT GCC     489
Val Pro Ala Met Tyr Val Ala Ile Gln Ala Val Leu Ser Leu Tyr Ala
130                 135                 140                 145

TCT GGC CGC ACG ACA GGC ATC GTC CTG GAT TCA GGT GAT GGC GTC ACC     537
Ser Gly Arg Thr Thr Gly Ile Val Leu Asp Ser Gly Asp Gly Val Thr
             150                 155                 160

CAC AAT GTC CCC ATC TAT GAA GGC TAT GCC CTG CCC CAT GCC ATC ATG     585
His Asn Val Pro Ile Tyr Glu Gly Tyr Ala Leu Pro His Ala Ile Met
         165                 170                 175

CGC CTG GAC TTG GCT GGC CGT GAC CTC ACG GAC TAC CTC ATG AAG ATC     633
Arg Leu Asp Leu Ala Gly Arg Asp Leu Thr Asp Tyr Leu Met Lys Ile
    180                 185                 190

CTC ACA GAG AGA GGC TAT TCC TTT GTG ACC ACA GCT GAG AGA GAA ATT     681
Leu Thr Glu Arg Gly Tyr Ser Phe Val Thr Thr Ala Glu Arg Glu Ile
195                 200                 205

GTG CGA GAC ATC AAG GAG AAG CTG TGC TAT GTG GCC CTG GAT TTT GAG     729
Val Arg Asp Ile Lys Glu Lys Leu Cys Tyr Val Ala Leu Asp Phe Glu
210                 215                 220                 225

AAT GAG ATG GCC ACA GCA GCT TCC TCT TCC TCC CTG GAG AAG AGC TAT     777
Asn Glu Met Ala Thr Ala Ala Ser Ser Ser Ser Leu Glu Lys Ser Tyr
             230                 235                 240

GAG CTG CCA GAT GGG CAG GTT ATC ACC ATT GGC AAT GAG CGC TTC CGC     825
Glu Leu Pro Asp Gly Gln Val Ile Thr Ile Gly Asn Glu Arg Phe Arg
         245                 250                 255
```

```
GTC CCT GAG ACC CTC TTC CAG CCT TCC TTT ATT GGC ATG GAG TCC GCT      873
Val Pro Glu Thr Leu Phe Gln Pro Ser Phe Ile Gly Met Glu Ser Ala
        260                 265                 270

GGA ATT CAT GAG ACA ACC TAC AAT TCC ATC ATG AAG TGT GAC ATT GAC      921
Gly Ile His Glu Thr Thr Tyr Asn Ser Ile Met Lys Cys Asp Ile Asp
    275                 280                 285

ATC CGT AAG GAC TTA TAT GCC AAC AAT GTC CTC TCT GGG GGC ACC ACC      969
Ile Arg Lys Asp Leu Tyr Ala Asn Asn Val Leu Ser Gly Gly Thr Thr
290                 295                 300                 305

ATG TAC CCT GGC ATT GCT GAC AGG ATG CAG AAG GAG ATC ACA GCC CTG     1017
Met Tyr Pro Gly Ile Ala Asp Arg Met Gln Lys Glu Ile Thr Ala Leu
                310                 315                 320

GCC CCC AGC ACC ATG AAG ATC AAG ATT ATT GCT CCC CCA GAG CGG AAG     1065
Ala Pro Ser Thr Met Lys Ile Lys Ile Ile Ala Pro Pro Glu Arg Lys
            325                 330                 335

TAC TCA GTC TGG ATC GGG GGC TCT ATC CTG GCC TCT CTC TCC ACC TTC     1113
Tyr Ser Val Trp Ile Gly Gly Ser Ile Leu Ala Ser Leu Ser Thr Phe
        340                 345                 350

CAG CAG ATG TGG ATC AGC AAG CCT GAG TAT GAT GAG GCA GGG CCC TCC     1161
Gln Gln Met Trp Ile Ser Lys Pro Glu Tyr Asp Glu Ala Gly Pro Ser
    355                 360                 365

ATT GTC CAC AGG AAG TGC TTC TAA A GTCAGAACAG GTTCTCCAAG             1206
Ile Val His Arg Lys Cys Phe *
370                 375

GATCCCCTCG AGACTACTCT GTTACCAGTC ATGAAACATT AAAACCTACA AGCCTTAAAA   1266

AAAAAAAAA                                                          1275
```

( 2 ) INFORMATION FOR SEQ ID NO:2:

( i ) SEQUENCE CHARACTERISTICS:
        ( A ) LENGTH: 376 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Cys Glu Glu Glu Thr Thr Ala Leu Val Cys Asp Asn Gly Ser Gly
1               5                   10                  15

Leu Cys Lys Ala Gly Phe Ala Gly Asp Asp Ala Pro Arg Ala Val Phe
            20                  25                  30

Pro Ser Ile Val Gly Arg Pro Arg His Gln Gly Val Met Val Gly Met
        35                  40                  45

Gly Gln Lys Asp Ser Tyr Val Gly Asp Glu Ala Gln Ser Lys Arg Gly
    50                  55                  60

Ile Leu Thr Leu Lys Tyr Pro Ile Glu His Gly Ile Ile Thr Asn Trp
65                  70                  75                  80

His Asp Met Glu Lys Ile Trp His His Ser Phe Tyr Asn Glu Leu Arg
                85                  90                  95

Val Ala Pro Glu Glu His Pro Thr Leu Leu Thr Glu Ala Pro Leu Asn
            100                 105                 110

Pro Lys Ala Asn Arg Glu Lys Met Thr Gln Ile Met Phe Glu Thr Phe
        115                 120                 125

Asn Val Pro Ala Met Tyr Val Ala Ile Gln Ala Val Leu Ser Leu Tyr
    130                 135                 140

Ala Ser Gly Arg Thr Thr Gly Ile Val Leu Asp Ser Gly Asp Gly Val
145                 150                 155                 160

Thr His Asn Val Pro Ile Tyr Glu Gly Tyr Ala Leu Pro His Ala Ile
```

|   |   |   |   |   |   |   |   |   |   |   |   |   |   |   |
|---|---|---|---|---|---|---|---|---|---|---|---|---|---|---|
| | | | | 165 | | | | 170 | | | | 175 | | |
| Met | Arg | Leu | Asp 180 | Leu | Ala | Gly | Arg | Asp 185 | Leu | Thr | Asp | Tyr | Leu 190 | Met | Lys |
| Ile | Leu | Thr 195 | Glu | Arg | Gly | Tyr | Ser 200 | Phe | Val | Thr | Thr | Ala 205 | Glu | Arg | Glu |
| Ile | Val 210 | Arg | Asp | Ile | Lys | Glu 215 | Lys | Leu | Cys | Tyr | Val 220 | Ala | Leu | Asp | Phe |
| Glu 225 | Asn | Glu | Met | Ala | Thr 230 | Ala | Ala | Ser | Ser | Ser 235 | Ser | Leu | Glu | Lys | Ser 240 |
| Tyr | Glu | Leu | Pro | Asp 245 | Gly | Gln | Val | Ile | Thr 250 | Ile | Gly | Asn | Glu | Arg 255 | Phe |
| Arg | Val | Pro | Glu 260 | Thr | Leu | Phe | Gln | Pro 265 | Ser | Phe | Ile | Gly | Met 270 | Glu | Ser |
| Ala | Gly | Ile 275 | His | Glu | Thr | Thr | Tyr 280 | Asn | Ser | Ile | Met | Lys 285 | Cys | Asp | Ile |
| Asp | Ile 290 | Arg | Lys | Asp | Leu | Tyr 295 | Ala | Asn | Asn | Val | Leu 300 | Ser | Gly | Gly | Thr |
| Thr 305 | Met | Tyr | Pro | Gly | Ile 310 | Ala | Asp | Arg | Met | Gln 315 | Lys | Glu | Ile | Thr | Ala 320 |
| Leu | Ala | Pro | Ser | Thr 325 | Met | Lys | Ile | Lys | Ile 330 | Ile | Ala | Pro | Pro | Glu 335 | Arg |
| Lys | Tyr | Ser | Val 340 | Trp | Ile | Gly | Gly | Ser 345 | Ile | Leu | Ala | Ser | Leu 350 | Ser | Thr |
| Phe | Gln | Gln 355 | Met | Trp | Ile | Ser | Lys 360 | Pro | Glu | Tyr | Asp | Glu 365 | Ala | Gly | Pro |
| Ser | Ile | Val 370 | His | Arg | Lys | Cys 375 | Phe | | | | | | | | |

( 2 ) INFORMATION FOR SEQ ID NO:3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CATGACTGGT AACAGAGTAG T   21

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

AGAGCGGAAG TACTCAGTCT G   21